US007091416B1

(12) United States Patent
Tsentr et al.

(10) Patent No.: US 7,091,416 B1
(45) Date of Patent: Aug. 15, 2006

(54) COVER ASSEMBLY FOR VIDEO MONITOR

(75) Inventors: Michael M. Tsentr, Solon, OH (US); Bernard J. Moss, Perry, OH (US); Michael J. Heser, Willoughby, OH (US); Justin J. Ymana, South Euclid, OH (US)

(73) Assignee: Steris Inc., Temecula, CA (US)

( * ) Notice: Subject to any disclaimer, the term of this patent is extended or adjusted under 35 U.S.C. 154(b) by 0 days.

(21) Appl. No.: 11/323,860

(22) Filed: Dec. 30, 2005

(51) Int. Cl.
*H02G 3/14* (2006.01)

(52) U.S. Cl. .......................... 174/66; 174/67; 248/324; 439/537; 362/147

(58) Field of Classification Search .................. 174/66, 174/67; 220/241, 242; 362/395, 147, 421; 439/537, 527; 248/324, 917
See application file for complete search history.

(56) References Cited

U.S. PATENT DOCUMENTS

| 4,710,819 | A | 12/1987 | Brown ........................ 358/229 |
| 4,963,903 | A | 10/1990 | Cane ........................... 354/81 |
| 5,867,210 | A | 2/1999 | Rod ............................. 348/51 |
| 6,096,025 | A | 8/2000 | Borders ........................ 606/1 |
| 6,328,458 | B1 | 12/2001 | Bell et al. .................... 362/371 |
| 6,402,351 | B1 | 6/2002 | Borders et al. ............. 362/395 |
| 6,431,515 | B1 * | 8/2002 | Gampe et al. .............. 248/324 |
| 6,464,383 | B1 | 10/2002 | Northington et al. ....... 362/572 |
| 6,471,363 | B1 | 10/2002 | Howell et al. ................ 362/11 |
| 6,610,054 | B1 * | 8/2003 | Edwards et al. .............. 606/41 |
| 6,715,269 | B1 | 4/2004 | Nanlawala et al. .......... 56/10.2 |
| 6,743,046 | B1 | 6/2004 | Rus ............................. 439/537 |
| 6,817,585 | B1 | 11/2004 | Wagner et al. .............. 248/324 |
| 6,863,252 | B1 | 3/2005 | Bosson .................... 248/278.1 |
| 6,909,465 | B1 * | 6/2005 | Liang ......................... 348/373 |
| 6,967,632 | B1 | 11/2005 | Minami et al. .............. 345/1.3 |
| 6,979,328 | B1 * | 12/2005 | Baerveldt et al. ............. 606/41 |

* cited by examiner

*Primary Examiner*—Dhiru R. Patel
(74) *Attorney, Agent, or Firm*—Kusner & Jaffe; Michael A. Centanni

(57) ABSTRACT

A cover assembly for enclosing data connections on a monitor that is mounted to a tubular support arm that has data cables extending therethrough. The cover assembly includes a sleeve surrounding a portion of the tubular support arm. The sleeve defines a passage between the sleeve and the tubular support arm for the cables to extend therethrough. A shield is connected to the second end of the tubular support arm. The shield has an arcuate outer surface with an aperture therethrough. The aperture is dimensioned to receive one end of the sleeve. A cover having an inner arcuate surface mounted to the monitor to be movable therewith. The cover encloses the shield with the arcuate outer surface of the shield facing the arcuate inner surface of the cover. The sleeve extends through a slot in the cover, wherein the monitor is rotatable about a first axis and further is rotatable about a second axis that is perpendicular to the first axis.

15 Claims, 11 Drawing Sheets

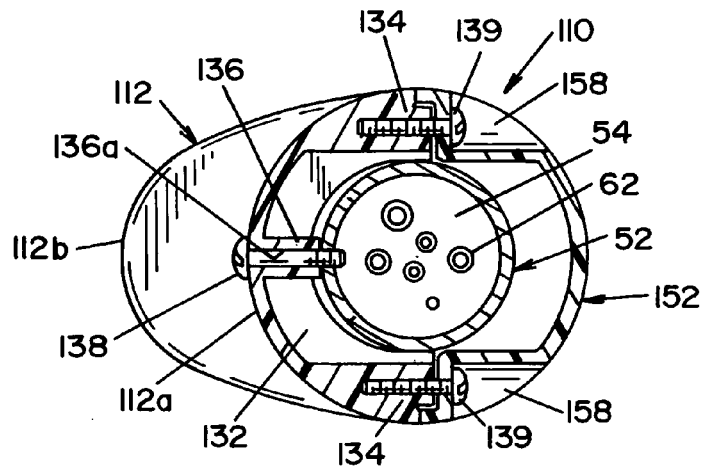
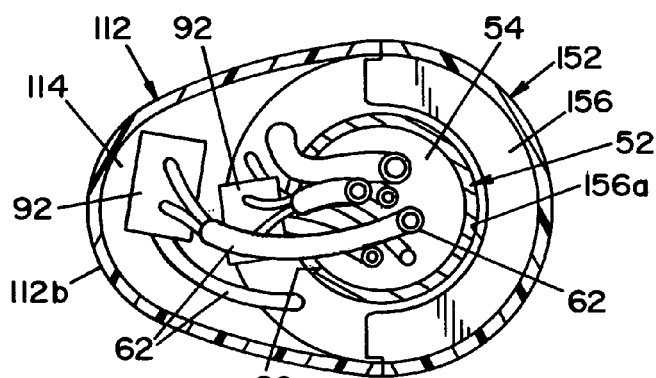
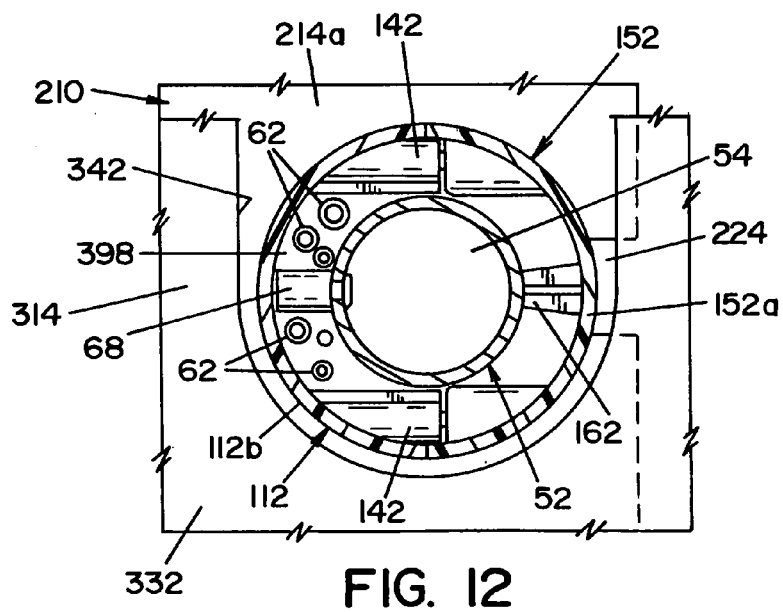

COVER ASSEMBLY FOR VIDEO MONITOR

FIELD OF THE INVENTION

The present invention relates generally to a ceiling mounted system for use in a surgical theater, and more particularly, to a cover assembly for mounting to an electrical device suspended from a ceiling-mounted support arm for enclosing electrical connections to the electrical device. The present invention is particularly applicable to a cover assembly for a video monitor used in a surgical theater, and shall be described with particular reference thereto. However, it will be appreciated that a cover assembly, according to the present invention, may find advantageous application with other devices used in a surgical theater, such as a video camera, surgical lights and control panels.

BACKGROUND OF THE INVENTION

Video monitors are used in surgical theaters to display information relating to a patient's physical condition, and to display images produced by a camera, such as for example, an endoscopic camera, used during medical procedures. Such monitors are typically mounted to tubular support arms that are suspended from a ceiling mount. U.S. Pat. Nos. 6,817,585 and 6,743,046 disclose examples of a ceiling-mounted light and monitor systems for use in a surgical theater.

Data transfer cables and wires are connected to the monitor through the tubular support arm. These data cables and wires exit the arm near the monitor for connection to connectors on the back of the monitor. The exposed data wires and cables, i.e., the portion of the data wires and cables outside the tubular support arm, must be sufficiently long to allow articulation of the monitor. In this respect, it is desirable to mount the monitor to the support arm so as to allow the monitor to be rotated between a landscaped position and a portrait position, so as to allow information and images to be displayed in different ways. It is further desirable that the monitor be able to tilt forward and back to optimize viewing orientation for the surgical staff. One problem with the exposed wires and electrical connections is that it is difficult to sterilize, disinfect or clean the individual cables and wires after a medical procedure.

The present invention provides a cover for enclosing the electrical connection on the back side of a video monitor suspended by a support arm, and at the same time, allows articulated motion of the electrical device relative to the support arm.

SUMMARY OF THE INVENTION

In accordance with a preferred embodiment of the present invention, there is provided a device for use in a surgical theater having a tubular support arm that has a first end and a second end. The first end is connected to a ceiling support structure. The tubular support arm has an opening near the second end. A sleeve surrounds the tubular support arm and covers the opening. The sleeve defines a passageway between the sleeve and the tubular support arm that communicates with the opening. A shield is connected to the second end of the tubular support arm. The shield has an arcuate outer surface with an aperture therethrough. The aperture is dimensioned to receive one end of the sleeve. An electrical device is attached to the second end of the support arm. The electrical device is rotatable about a first axis, and further is rotatable about a second axis that is perpendicular to the first axis. Data cables extend through the tubular support arm. The cables extend through the opening near the second end of the tubular support arm and through the passageway in the sleeve for attachment to the electrical device. A cover having an inner arcuate surface is mounted to the electrical device to be movable therewith. The cover encloses the shield with the arcuate outer surface of the shield facing the arcuate inner surface of the cover. The cover has an elongated slot formed in the arcuate inner surface. The sleeve extends through the slot, wherein the shield and the cover are movable relative to each other and the shield and cover form a cavity containing the data cables and connections to the electrical device.

In accordance with another embodiment of the present invention, there is provided a cover assembly for enclosing data connections on a motor that is mounted to a tubular support arm that has data cables extending therethrough. The cover assembly includes a sleeve surrounding the tubular support arm and covering the data cables where the cables exit the tubular support arm. The sleeve defines a passage between the sleeve and the tubular support arm for a portion of the cables to extend therethrough. A shield is connected to the second end of the tubular support arm. The shield has an arcuate outer surface with an aperture therethrough. The aperture is dimensioned to receive one end of the sleeve. A cover having an inner arcuate surface is mounted to the monitor to be movable therewith. The cover encloses the shield with the arcuate outer surface of the shield facing the arcuate inner surface of the cover. The cover has an elongated slot formed in the arcuate inner surface. The sleeve extends through the slot, wherein the monitor is rotatable about a first axis and further is rotatable about a second axis that is perpendicular to the first axis. The connections between the data cables and the monitor are contained within a cavity defined by the shield and the cover.

It is an advantage of the present invention to provide a cover assembly for covering electrical connections to an electrical device mounted on a support arm.

Another advantage of the present invention is a cover assembly as described above for covering electrical connections to a ceiling-mounted electrical device used in a surgical theater.

Another advantage of the present invention is a cover assembly as described above for covering the electrical connections to a ceiling-mounted monitor used in a surgical theater.

Another advantage of the present invention is a cover assembly as described above which allows articulated movement of the electrical device relative to the support arm.

Yet another advantage of the present invention is a cover assembly as described above that is easy to clean.

A still further advantage of the present invention is a cover assembly as described above that includes mounting means for mounting individual cables to avoid kinking or crimping of the cables during movement of the electrical device.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein:

FIG. 10 is a sectional view taken along lines 10—10 of FIG. 9;

FIG. 11 is a sectional view taken along lines 11—11 of FIG. 9;

FIG. 12 is a sectional view taken along lines 12—12 of FIG. 9; and

DETAILED DESCRIPTION OF PREFERRED EMBODIMENT

Figure 1:
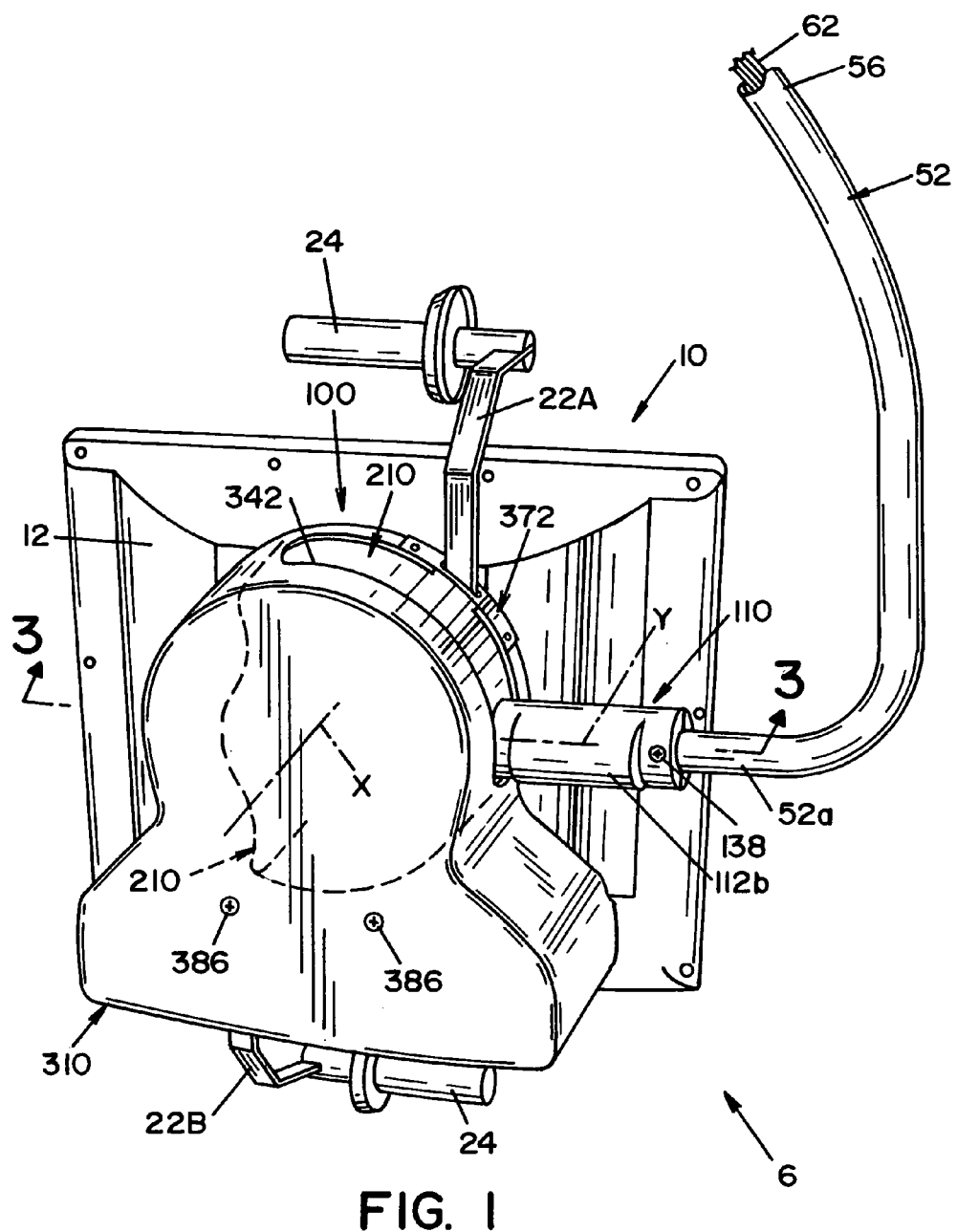
FIG. 1 is a perspective view of a cover assembly, according to the present invention, for use on the back of a video monitor that is supported by a support arm, showing the cover assembly in a first position when the video monitor is in a landscape orientation.
Figure 3:
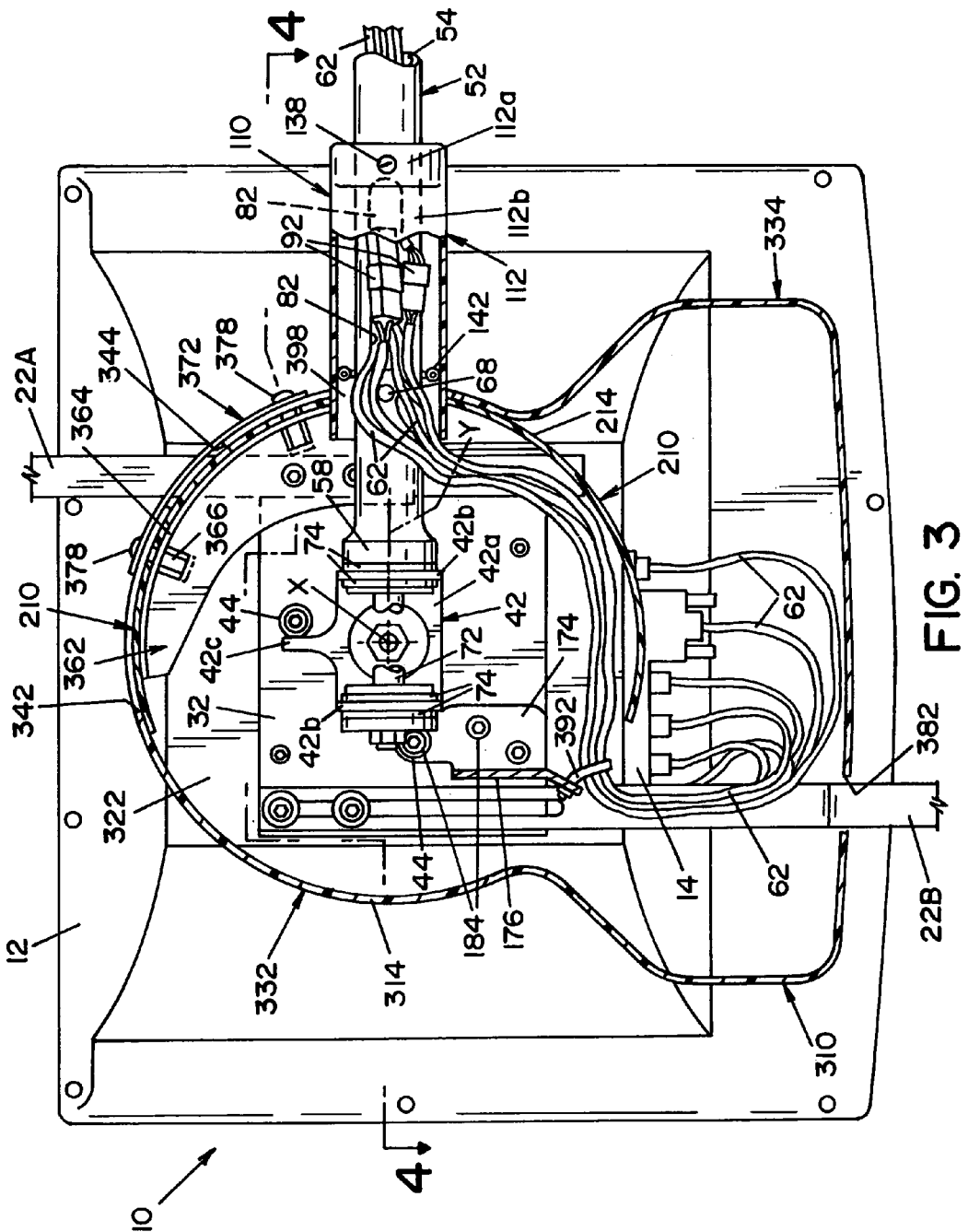
FIG. 3 is a sectional view taken along lines 3—3 of FIG. 1.

Referring now to the drawings wherein the showings are for the purpose of illustrating a preferred embodiment of the invention only, and not for the purpose of limiting same, FIG. 1 shows a device 6 for use in a surgical theater, comprised of a video monitor 10, a support arm 52 and a cover assembly 100, illustrating a preferred embodiment of the present invention. Monitor 10 (shown from the backside) has a back panel 12 that includes a row of data ports or connections 14, best seen in FIG. 3. A pair of handle arms 22A, 22B is attached to monitor 10. In the embodiment shown, handle arms 22A, 22B are flat, thin bars that are mounted to monitor 10, as best seen in FIG. 3. Handle arms 22A, 22B extend in opposite directions from monitor 10. Handgrips 24 are provided on the free ends of handle arms 22A, 22B.

Monitor 10 includes a rigid, mounting plate 32 that is fixedly secured to the backside of monitor 10. A hinge bracket 42 is attached to mounting plate 32 such that hinge bracket 42 is rotatable relative to mounting plate 32 about a first axis "X," as best seen FIG. 3. Hinge bracket 42 is generally U-shaped and includes a generally flat base portion 42a, and a pair of spaced-apart side portions 42b that extend from base portion 42a. An arm 42c extends to one side of base portion 42a, as shown in FIG. 3. Stops 44 are attached to mounting plate 32 to engage arm 42c and to limit rotation of hinge bracket 42 to about 90 angular degrees.

Figure 2:
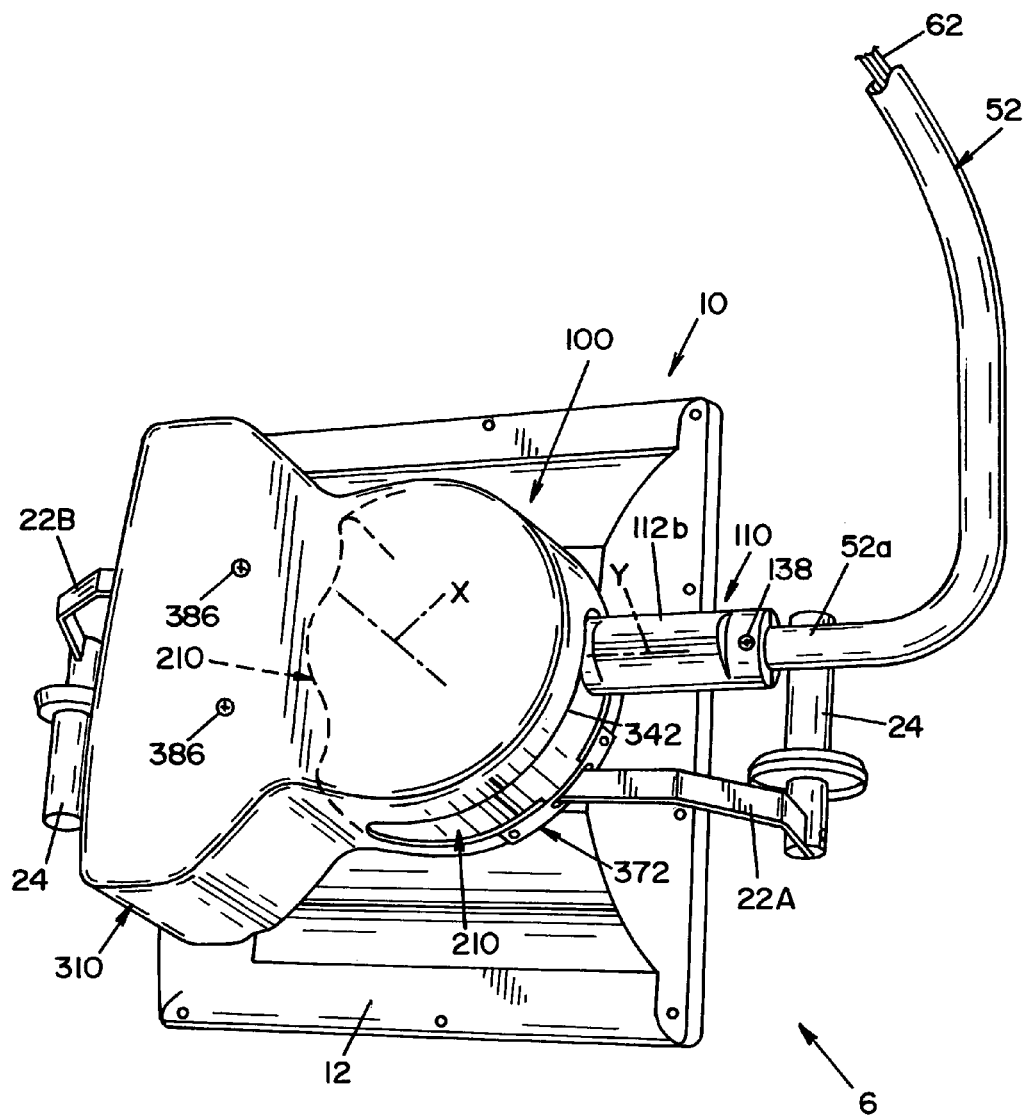
FIG. 2 is a perspective view of the cover assembly shown in FIG. 1, showing the cover assembly in a second position when the video monitor in a pictorial orientation.

A support arm 52, best seen in FIGS. 1 and 2, is attached to hinge bracket 42. In the embodiment shown, support arm 52 is part of a ceiling-mounted system (not shown) of the type disclosed in U.S. Pat. Nos. 6,817,585 and 6,743,046, the disclosures of which are expressly incorporated herein by reference. Support arm 52 is tubular and defines an inner passage 54 through which data carrying cables and wires 62 (hereinafter referred to as "data cables 62") are arranged. As used herein, the term "data cables 62" shall refer to copper and metal cables and wires, as well as fiber optic cables and fibers that can convey data in analog, digital, electrical or light forms.

Figure 4:
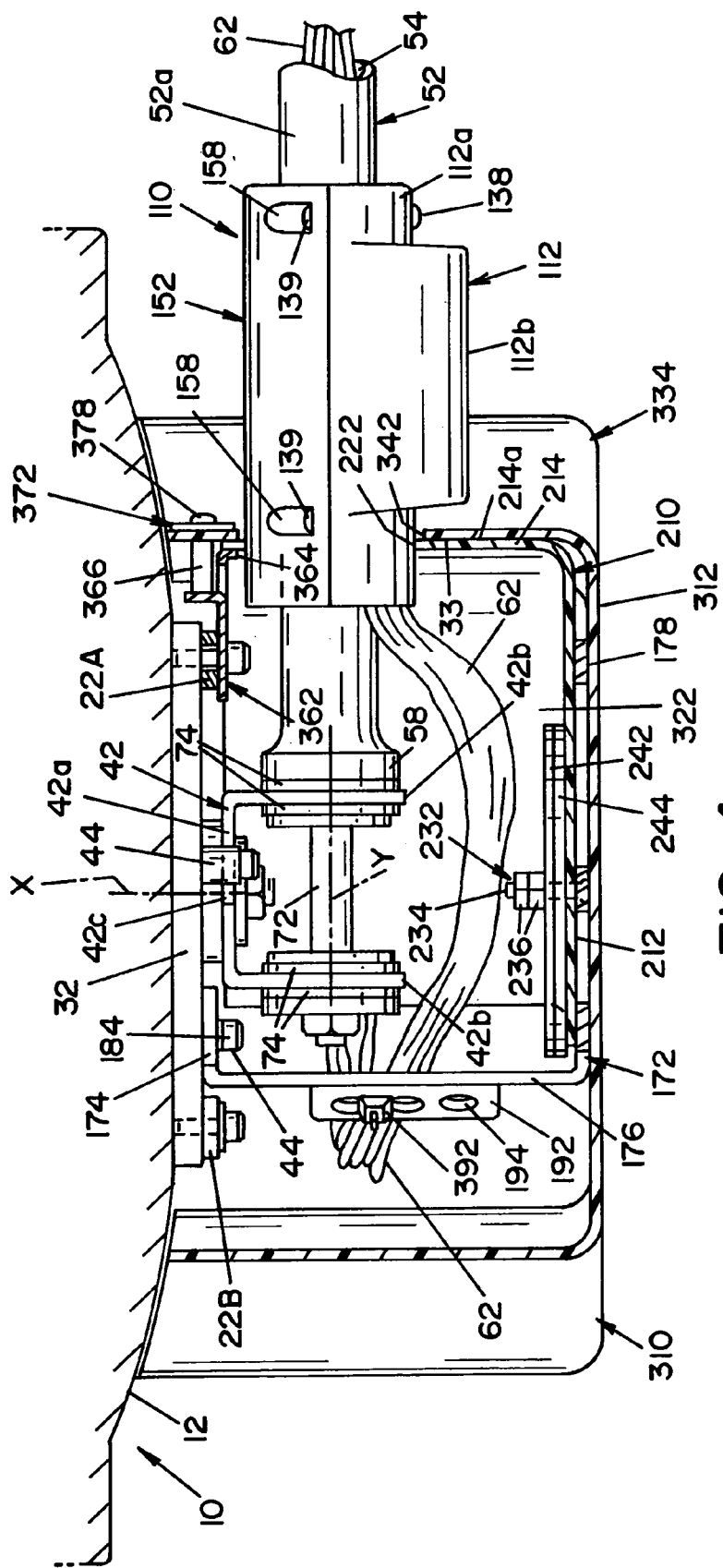
FIG. 4 is a sectional view taken along lines 4—4 of FIG. 3.

Support arm 52 is tubular and includes a straight section 52a. Support arm 52 has a first end 56 that is connected to a hub on a ceiling-mounted device (not shown) and a second, free end 58. Second end 58 of support arm 52, best seen in FIG. 4, includes a mounting pin 72. Mounting pin 72 is fixedly secured to second end 58 of support arm 52 and extends therefrom along a second axis "Y" of straight section 52a of tubular support arm 52. In the embodiment shown, axis "Y" is perpendicular to axis "X," as best seen in FIGS. 3 and 4. Mounting pin 72 extends through openings in side portions 42b of hinge bracket 42, wherein hinge bracket 42 (and monitor 10 that is attached thereto) is pivotable about axis "Y" of mounting pin 72. Friction plates 74 are disposed on mounting pin 72 on opposite sides of side portions 42b of mounting bracket 42, such that monitor 10 is movable and positionable to any desired position, in a conventionally known manner.

Figure 9:
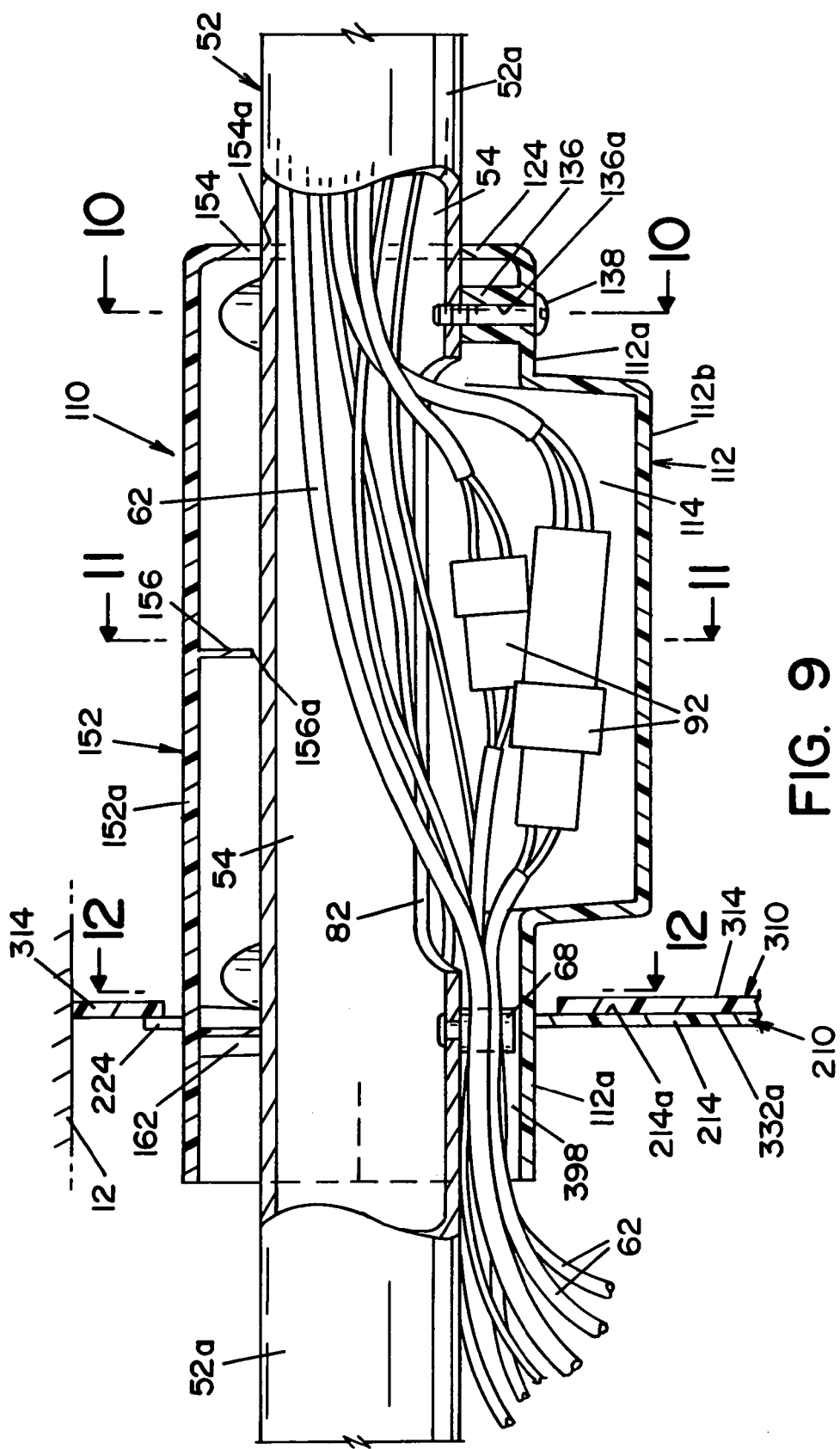
FIG. 9 is a sectional view of a portion of a support arm and a sleeve that is attached thereto.

An elongated slot or opening 82 is formed in tubular support arm 52, as best seen in FIGS. 3 and 9. Data cables 62 exit passage 54 in tubular support arm 52 through elongated slot or opening 82 to allow for connection to data connectors and ports 14 on monitor 10, as illustrated in FIG. 3. As shown in FIG. 9, cable connections 92 are sometimes made where data cables 62 exit tubular support arm 52.

Figure 7:
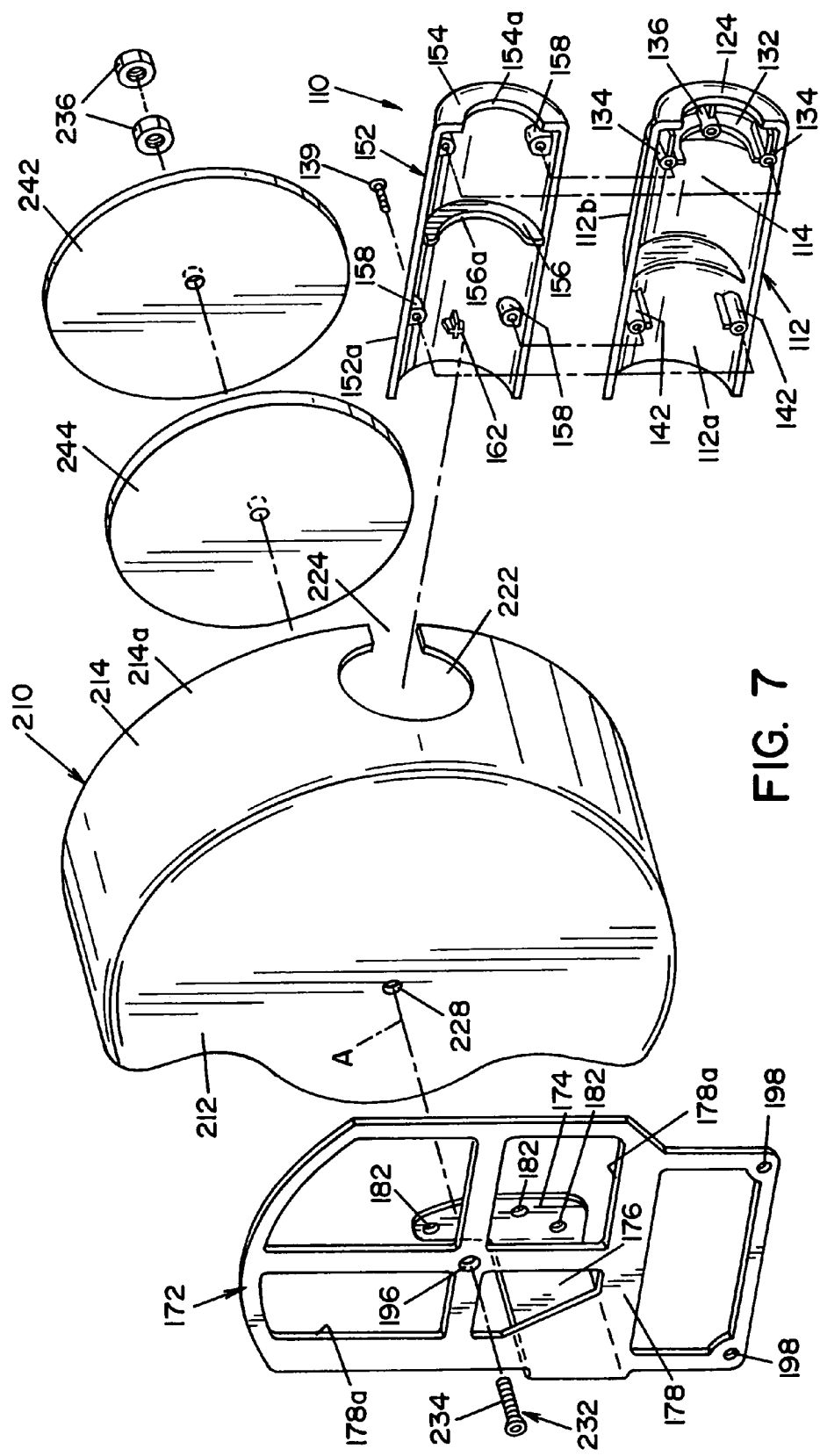
FIG. 7 is an exploded view showing the mounting bracket and shield shown in FIG. 6, together with a sleeve that is connected to the shield.
Figure 13:
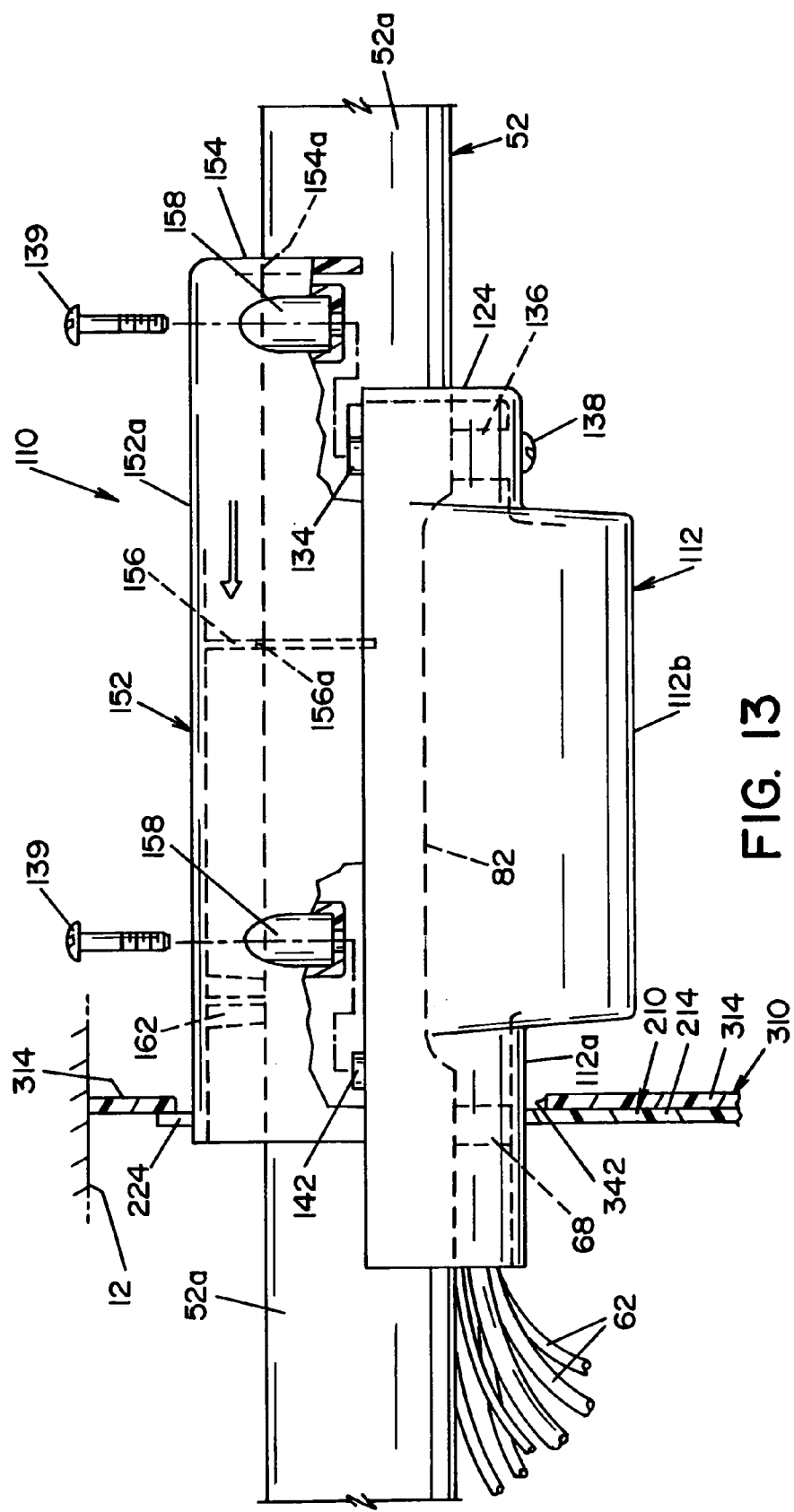
FIG. 13 is an elevational view of the sleeve illustrating how the sleeve is connected to the shield and cover of the cover assembly.

Cover assembly 100 is basically comprised of a sleeve 110, a shield 210 and a cover 310. Sleeve 110 is provided to be mounted to support arm 52 and to enclose elongated slot or opening 82 and data cables 62 extending therefrom. Sleeve 110, best seen in FIGS. 9–13, includes a first sleeve section 112 that is attachable to tubular support arm 52, and a second sleeve section 152 that is attachable to first sleeve section 112. First sleeve section 112 has a main body portion 112a that is shaped as half a cylinder. An outwardly extending projection or hump 112b, best seen in FIG. 3, is formed in body portion 112a of first sleeve section 112. Projection or hump 112b forms an interior cavity 114, best seen in FIG. 9. First sleeve section 112 has a first end with an inwardly extending flange 124. Flange 124 has an arcuate, inner edge that is dimensioned to mate with and to abut the outer surface of tubular support arm 52. A wall section 132 is formed along the inner surface of body portion 112a of first sleeve section 112, as best seen in FIG. 7. Wall section 132 is spaced from flange 124 and has an inner edge that is shaped to generally conform to the outer surface of tubular support arm 52. As best seen in FIGS. 7 and 10, two outer posts or bosses 134 are integrally formed within wall section 132 at the ends thereof. An intermediate post 136 is formed in wall section 132 between posts 134. Intermediate post 136, best seen in FIGS. 9 and 10, has an opening 136a therethrough. Opening 136a is dimensioned to receive a fastener 138 that secures first sleeve section 112 to tubular support arm 52, as shall be discussed in greater detail below. In the embodiment shown, fastener 138 is a cap screw that extends into a threaded hole formed in tubular support arm 52 near one end of elongated slot 82. Outer posts 134 are disposed at the extreme ends of wall section 132. As best seen in FIGS. 10 and 13, these outer posts 134 extend slightly beyond the edge of first sleeve section 112. An additional pair of mounting posts 142 is provided near the second end of first sleeve section 112. Like outer post 134, additional mounting posts 142 project slightly above the edges of first sleeve section 112, as best seen in FIGS. 12 and 13.

Second sleeve section 152 is dimensioned to mate with first sleeve section 112. In this respect, in the embodiment shown, second sleeve section 152 has a body portion 152*a* having a shape in the form of half a cylinder. Second sleeve section 152 has an inwardly extending flange 154 formed at one end of body portion 152*a*. Flange 154 has an inner edge 154*a* dimensioned to abut and conform to the outer surface of tubular support arm 52. Second sleeve section 152 has a reinforcing wall 156 formed along the inner surface thereof, as best seen in FIG. 7. Reinforcing wall 156 has an inner edge 156*a* dimensioned to conform to the shape of the exterior surface of tubular support arm 52. The distal ends of reinforcing wall 156 extend slightly above the edges of second sleeve section 152, as best seen in FIG. 11. Second sleeve section 152 is formed to include a plurality of spaced-apart recesses or cavities 158, best seen in FIG. 13. Recesses 158 are generally cylindrical in shape, and are dimensioned to receive fasteners to attach second sleeve section 152 to first sleeve section 112. In this respect, recesses 158 in second sleeve section 152 are disposed to be in registry with mounting posts 134, 142 on first sleeve section 112. A spacing element 162 is formed on the inner surface of second sleeve section 152. Spacing element 162 is dimensioned to abut the outer surface of tubular support arm 52, as illustrated in FIG. 12, and to position body portion 152*a* of sleeve section 152 relative to support arm 52.

Figure 5:
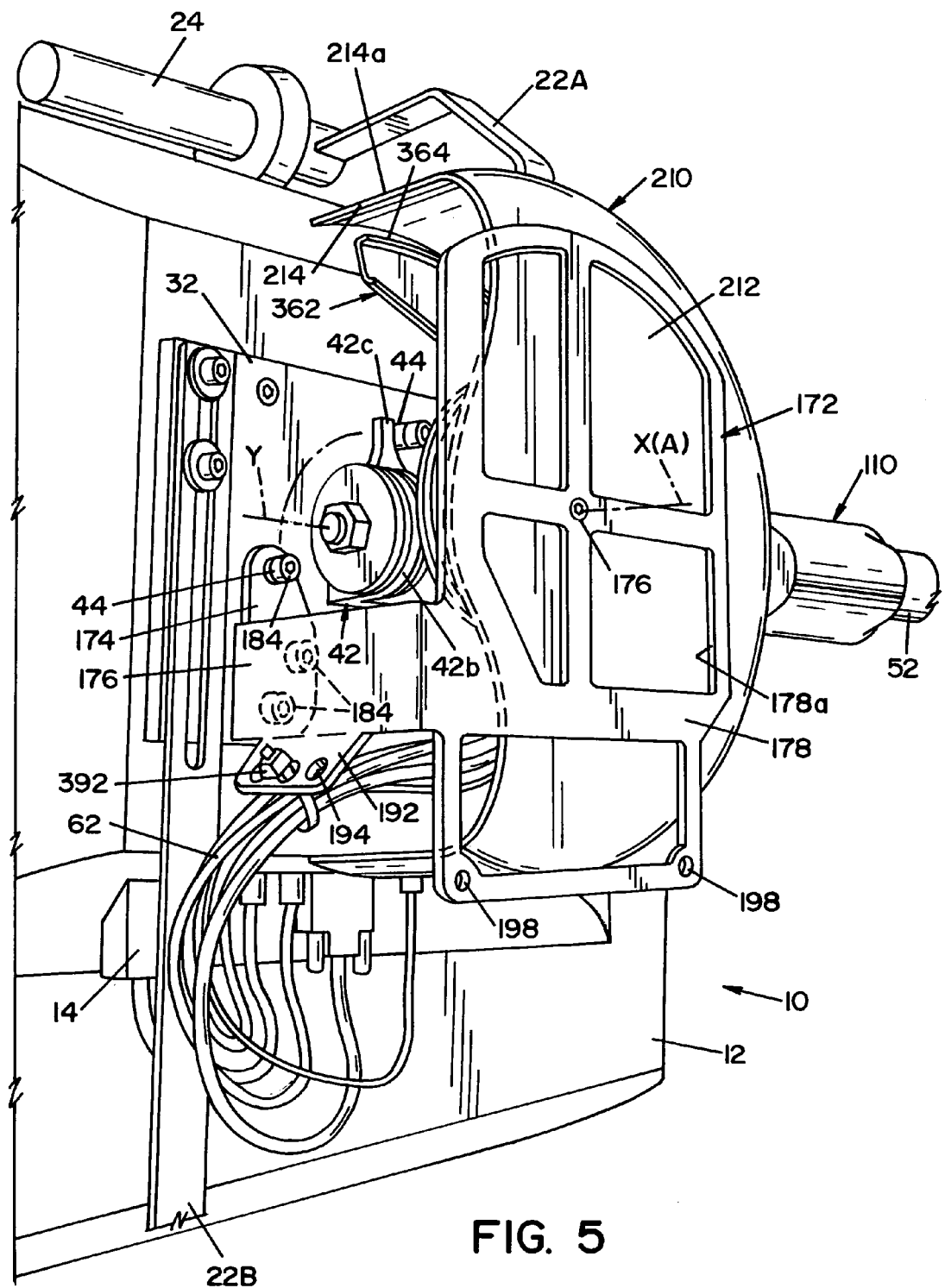
FIG. 5 is a perspective view of the cover assembly shown in FIG. 1, showing the cover assembly with an outer cover removed therefrom.

Referring now to FIGS. 5 and 7, shield 210 is best seen. Shield 210 is designed to be mounted onto monitor 10, and to be connected to support arm 52, such that shield 210 remains stationary relative to tubular support arm 52 as monitor 10 moves relative thereto about axis "X." Shield 210 is attached to a mounting bracket 172, best seen in FIGS. 5 and 7. Mounting bracket 172 includes a planar base portion 174, a side portion 176 extending from base portion 174, and a window-like or web-like face portion 178 that is attached to side portion 176. Mounting bracket 172 is preferably integrally formed of a rigid material. Base portion 174 includes a plurality of apertures 182. Apertures 182 are dimensioned to receive conventional fasteners 184 for securing base portion 174 of mounting bracket 172 to mounting plate 32 on monitor 10. One aperture 182 receives a fastener 184 having a stop 44 mounted thereon, as mentioned above and that shall be described in greater detail below.

Side portion 176 of mounting bracket 172 is a flat strip that extends from base portion 174. Side portion 176 includes an angled tab 192 having a plurality of apertures 194 formed therein, as best seen in FIG. 5. Face portion 178 of mounting bracket 172 is a planar structure having a window-frame-like configuration. Openings 178*a* in face portion 178 are to reduce the overall weight of mounting bracket 172. An opening 196 is located generally in the center of the planar face portion 178 of mounting bracket 172. Two other openings 198 are disposed along the periphery of planar face portion 178 of mounting bracket 172, as best seen in FIG. 7.

Shield 210, best seen in FIG. 7, is generally a cup-shaped structure having a face portion 212 and a side wall portion 214. Side wall portion 214 is generally cylindrical in shape and extends along an arc about a central axis, designated "A" in FIG. 7. Side wall portion 214 spans a circular arc of approximately 200 angular degrees. Side wall portion 214 defines a generally cylindrical outer surface 214*a* that is symmetrical about axis "A." A circular hole 222 is formed in the side wall portion 214 of shield 210. Hole 222 is dimensioned to be slightly larger than the outer diameter of sleeve 110, so as to receive one end of sleeve 110 therein. A space or gap 224 extends to one side of hole 222 toward the free edge of shield 210. Gap 224 is dimensioned to facilitate the mounting of shield 210 onto support arm 52, as shall be described in greater detail below.

Shield 210 is dimensioned to be attached to mounting bracket 172. As shown in the drawing, shield 210 is disposed between planar face portion 178 of mounting bracket 172 and mounting plate 32 of monitor 10. Shield 210 is attached to face portion 178 of mounting bracket 172 by a conventional fastener 232 that is comprised of a bolt 234. Bolt 234 extends through central opening 196 in face portion 178 of mounting bracket 172 and through an aperture 228 in face portion 212 of shield 210. Aperture 228 in face portion 212 of shield 210 is disposed along axis "A." A rigid backing plate 242 and an intermediate friction disk 244 are mounted to one side of face portion 212 of shield 210, as illustrated in FIG. 7. Shield 210 is mounted to mounting bracket 172 to allow limited rotation of shield 210 about axis "A" of bolt 234 relative to mounting bracket 172 and monitor 10. In this respect, axis "A" of bolt 234 is coaxial with axis "X" of hinge bracket 42. The length of side wall portion 214 of shield 210 is dimensioned such that the free edge or end of side wall portion 214 does not engage monitor 10 so as to allow movement of shield 210 relative to monitor 10.

Figure 8:
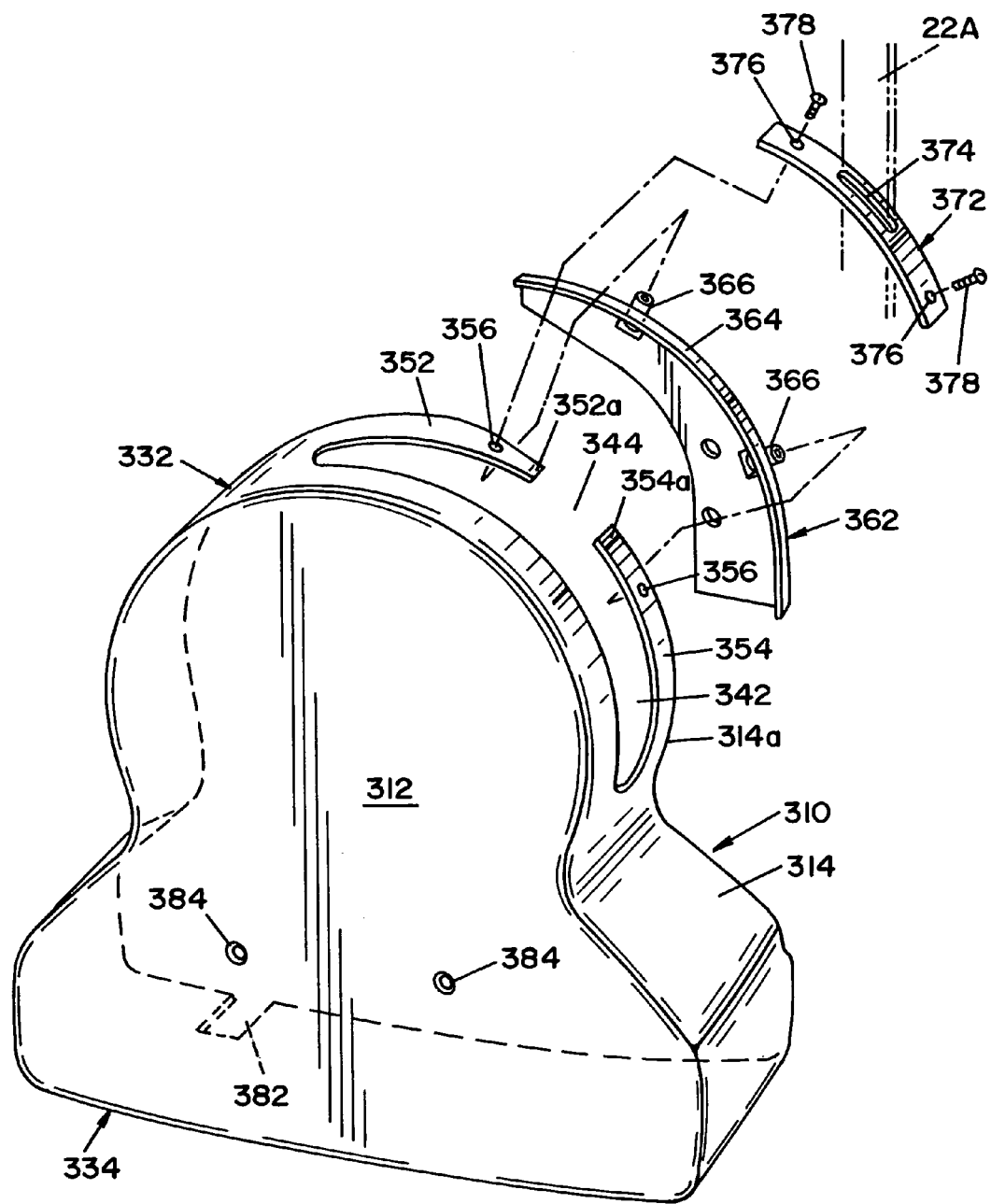
FIG. 8 is a perspective view of a cover and attachment components from the cover assembly shown in FIG. 1.

Referring now to FIG. 8, cover 310 is best seen. Cover 310 has a generally planar back wall 312 and a side wall 314 extending to one side of back wall 312 along the periphery thereof. The free edge 314*a* of side wall 314 is dimensioned to conform and mate with back panel 12 of monitor 10 to form a generally closed inner chamber or cavity 322 that is dimensioned to contain shield 210, mounting bracket 172 and data cables 62 that are connected to monitor 10.

Cover 310 has cylindrical portion 332 designed to receive and surround shield 210. Cylindrical portion 332 of cover 310 has an inner surface 332*a* dimensioned to closely match outer surface 214*a* of cylindrical side wall portion 214 of shield 210. Cylindrical portion 332 of cover 310 flares outwardly into a generally rectangular or trapezoidal region 334 that is dimensioned to enclose and cover the data ports 14 of monitor 10.

As best seen in FIG. 8, an elongated slot 342 is formed in side wall 314 of cylindrical portion 332. Slot 342 is dimensioned to be in registry with hole 222 in shield 210, when cover 310 is mounted to monitor 10. Slot 342 has a width generally equal to the diameter of sleeve 110, such that one end of sleeve 110 can extend therethrough. Slot 342 has a side opening 344 that extends through cylindrical side wall 314 to form two thin side wall panels 352, 354 having spaced-apart ends 352*a*, 354*a*. Openings 356 are formed in panels 352, 354.

An arcuate support 362 is mounted to mounting plate 32 of monitor 10. Arcuate support 362 has an arcuate flange or ledge surface 364, generally matching the arcuate shape of cylindrical portion 332 of cover 310. Arcuate support 362 includes threaded sleeves 366 that are mounted to one side of arcuate ledge surface 364, best seen in FIG. 4. An arcuate strap 372 is provided to span the gap defined between ends 352*a*, 354*a* of cover 310. The arcuate strap 372 includes an elongated slot 374 dimensioned to allow handle arm 22A to extend therethrough. An aperture 376 is formed at each end of strap 372. Apertures 376 are to receive conventional flat head screws 378 that extend through strap 372 and through panels 352, 354 into mounting posts 366 on arcuate support 362. In this respect, strap 372 covers the gap formed in cylindrical portion 332 of cover 310.

As best seen in FIG. 8, a notch 382 is provided in rectangular portion 334 of side wall 314 of cover 310. Notch 382 is dimensioned to allow handle portion 22B to extend therethrough, as illustrated in FIG. 3.

Cover 310 includes two spaced-apart, counter bored openings 384. Openings 384 are disposed on cover 310 to be in registry with openings 198 in face portion 178 of mounting bracket 172. In this respect, cover 310 is mounted to monitor 10 by conventional flat head screws 386 extending through cover 310 and threaded openings 198 in mounting bracket 172.

Sleeve 110, shield 210 and cover 310 are preferably formed of tough, resilient polymer material(s) that can be injection molded. By way of example and not limitation, sleeve 110, shield 210 and cover 310 may be formed of ABS (acrylonitrile butadiene styrene), a polyamide (nylon), a styrene-based polymer or PMMA (polymethyl methacrylate). In a preferred embodiment, sleeve 110, shield 210 and cover 310 are formed of ABS (acrylonitrile butadiene styrene). Shield 210 and cover 310 have a thickness of approximately 0.125 inches.

Figure 6:
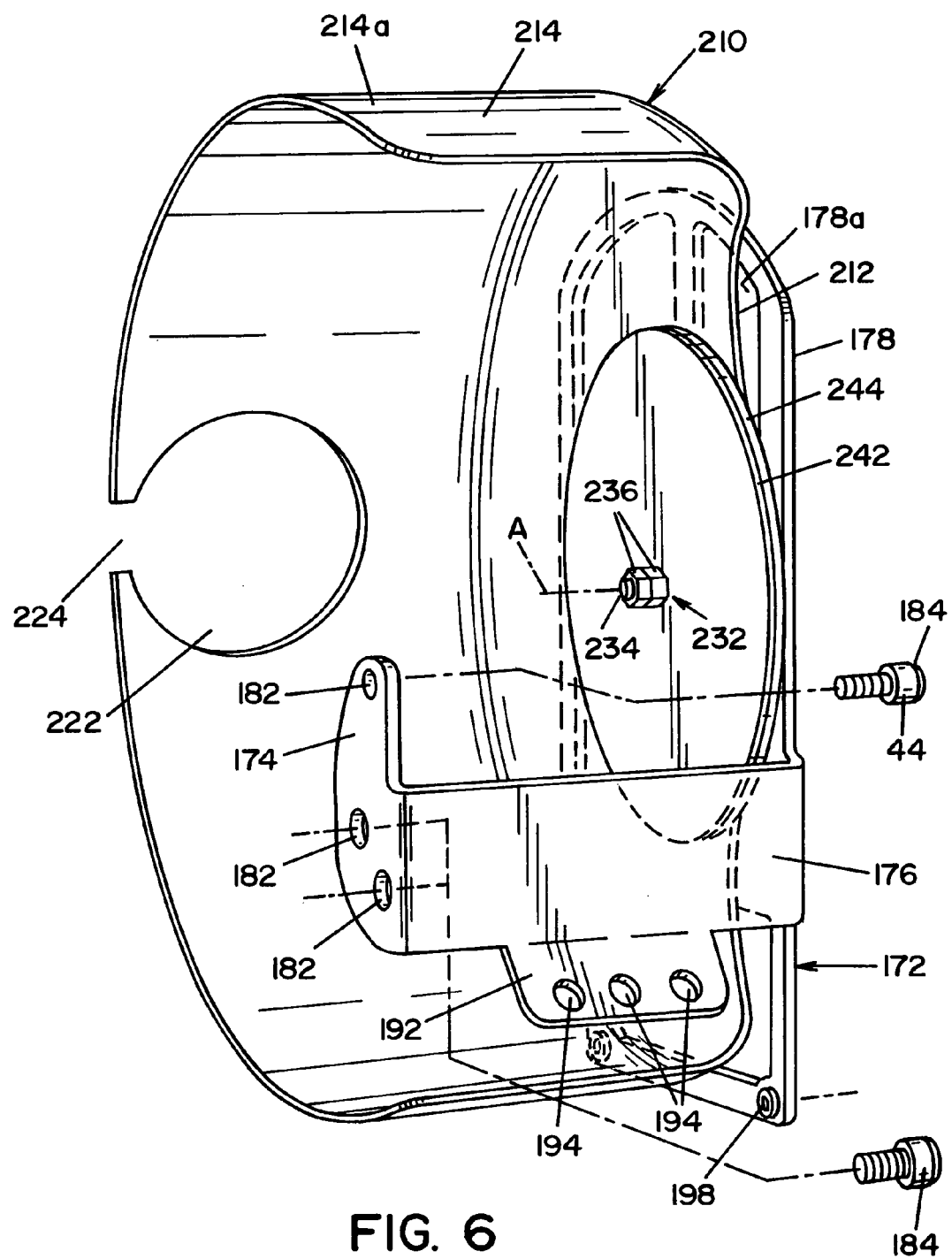
FIG. 6 is a view of a shield and mounting bracket from the cover assembly shown in FIG. 1.

Cover assembly 100 shall now be further described with respect to the assembly and use thereof. Monitor 10 is typically mounted to support arm 52 by mounting pin 72 extending through hinge bracket 42, as described above. Shield 210 is attached to mounting bracket 172 as shown in FIG. 6. In this respect, backing plate 242 and friction disk 244 are positioned against the inner side of face portion 212 of shield 210. Face portion 178 of mounting bracket 172 is positioned against the opposite side of face portion 212 of shield 210. Nuts 236 and bolt 234 extending through the apertures in mounting bracket 172, friction disk 244 and backing plate 242 secure the respective components together. Nuts 236 and bolt 234 are tightened to allow sliding movement of shield 210 relative to mounting bracket 172. Arcuate support 362 is attached to mounting plate 32 of monitor 10 by conventional fasteners. As best seen in FIG. 4, arcuate support 362 is positioned on handle arm 22A with fasteners extending through arcuate support 362 and handle arm 22A.

Mounting bracket 172 is attached to mounting plate 32 by fasteners 184. In the embodiment shown, fasteners 184 are hexagonal socket head screws. One of the socket head screws defines a stop 44, as best seen in FIG. 5. Data cables 62, for attachment to monitor 10, are secured to tab 192 on side portion 176 of mounting bracket 172. Data cables 62 are secured to tab 192 by conventional cable ties 392 to organize a position of data cables 62 relative to bracket 172 and relative to data ports 14 on the back of monitor 10.

Cover 310 is then mounted onto monitor 10. To this end, monitor 10 is moved to a position where slot 342 in side wall 314 is aligned with tubular support arm 52 such that cover 310 may be positioned onto mounting bracket 172 with support arm 52 moving into elongated slot 342 through opening 344 in the side wall 314 of cover 310. Cover 310 is fastened to mounting bracket 172 by means of fasteners extending through opening 384 and back wall 312 into threaded openings 198 and face portion 178 of mounting bracket 172.

As best seen in FIG. 3, handle arm 22B extends through notch 382 of cover 310. In this respect, handle arm 22A may be removed from back panel 12 of monitor 10 to allow strap 372 to be slid onto handle arm 22A, as illustrated in FIG. 8. Strap 372 is positioned over panels 352, 354 of cylindrical portion 332 of cover 310. Screws 378 extend through apertures 376 in strap 372 and through openings 356 in panels 352, 354. Screws 378 are fastened to threaded sleeves 366 on arcuate support 362. As best seen in FIG. 4, threaded sleeve 366 is dimensioned such that when panels 352, 354 and strap 372 are secured thereto, a space or gap exists between arcuate ledge 364 on arcuate support 362 and the inner surface of panels 352, 354. This space or gap is dimensioned to receive the free edge of side wall portion 214 of shield 210 so as to allow sliding of the free edge of shield 210 therein. As indicated above, in the embodiment shown, strap 372 is positioned over panels 352, 354 of cover 310. It is also contemplated that strap 372 can be positioned between cylindrical portion 332 of cover 310 and shield 210. In other words, strap 372 may be positioned under panel 352, 354.

As best shown in FIGS. 4 and 9, when cover 310 is mounted to monitor 10, the outer cylindrical surface of side wall portion 214 of shield 210 mates with the inner cylindrical surface of side wall 314 of cylindrical portion 332. As shown in the drawings, circular hole 222 and shield 210 are aligned with slot 342 and cover 310. Straight section 52a of support arm 52 extends through slot 342 in cover 310, and through circular hole 222 and shield 210.

With shield 210 and cover 310 in place on monitor 10, sleeve 110 is attached to tubular support arm 52. As best seen in FIG. 9, sleeve 110 is dimensioned such that one end thereof extends through slot 342 of cover 310 and through hole 222 and shield 210. First sleeve section 112 is dimensioned such that hump 112b is disposed in registry with elongated slot 82 and support arm 52. To position first sleeve section 112, first sleeve section 112 is placed against support arm 52. Flange 124 and internal wall section 132 allow first sleeve section 112 to be easily positioned against the cylindrical surface of support arm 52 and to slide therealong. Once first sleeve section 112 is slid into position, it is attached to support arm 52 by means of fastener 138 as best seen in FIGS. 9 and 10.

As seen in FIG. 9, a passageway 398 is defined between support arm 52 and first sleeve section 112. A spacer 68 is mounted to support arm 52. Spacer 68 maintains separation between first sleeve section 112 and support arm 52, and divides passageway 398 into two separate channels for data cables 62, as best seen in FIG. 12.

With first sleeve section 112 in place, second sleeve section 114 is positioned against support arm 52. Flange 154 and reinforcing wall 156 help locate second sleeve section 152 relative to support arm 52. In addition, posts 134 and 142 on first sleeve section 112, that extend beyond the edges of first body portion 112a, basically align second sleeve section 114 in relationship to the edge of first sleeve section 112, and allow the edges of second sleeve section 114 to slide along the edges of first sleeve section 112. Once the edges of second sleeve section 114 are aligned and mated with first sleeve section 112, second sleeve section 114 can be slid into position along support arm 52. In this respect, second sleeve section 114 is slid into position, wherein cavities 158 and second sleeve section 114 are aligned and in registry with posts 136, 142 on first sleeve section 112. Fasteners 139 are inserted into cavities 158 to secure second sleeve section 114 to first sleeve section 112, as illustrated in FIG. 10. As shown in the drawings, the cylindrical side wall of shield 210 is dimensioned to engage and slide along the inner surface of cylindrical portion 332 of cover 310. When cover assembly 100 is mounted to monitor 10, cover 310 is movable with monitor 10 relative to shield 210 and support arm 52. FIG. 1 shows cover assembly 100 in a first position where monitor 10 is in a "landscape" orientation. FIG. 2 shows cover assembly 100 in a second position when monitor 10 is a "pictorial" orientation. As illustrated in FIGS. 1 and 2, monitor 10 and cover 310 are moveable about axis "X" through hinge bracket 42. Elongated slot 342 in cover 310 allows cover 310 to slide over shield 210 and relative to support arm 52. Stops 44 limit relative movement of hinge bracket 42, and thus monitor 10 to about 90 angular degrees. More specifically, movement of arm 42c on hinge bracket 42 is limited by stops 44 such that monitor 10 is basically moveable between the landscape orientation and pictorial orientation shown in FIGS. 1 and 2.

As best seen in FIG. 5, when monitor 10 is in the landscape orientation, a gap or space is defined between the edge of shield 210 and side portion 176 of mounting bracket 172. Data cables 62 mounted to tab 192 on side portion 176 are disposed within the gap. In other words, shield 210 is designed so as not to interfere with data cables 62 during rotation of the monitor. Rotation of monitor 10 to a pictorial orientation basically widens the space or gap between the edge of shield 210 and side portion 176 of mounting bracket 172.

The present invention thus provides a cover assembly 100 for a support mounted electrical device, which cover assembly 100 encloses data cables 62 and connection ports 14 to the electrical device. The cover assembly allows for rotation of the electrical device relative to the support arm along two axes. Cover assembly 100 encloses the data cables to the electrical device thereby providing surfaces that are easier to clean following a procedure in a surgical theater. Still further, the cover assembly allows for easier connection between monitor harness cables and a universal cable bundle that may exist within the support arm.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A device for use in a surgical theater, comprising:
   a tubular support arm having a first end and a second end, said first end connected to a ceiling support structure, said tubular support arm having an opening near said second end;
   a sleeve surrounding said tubular support arm and covering said opening, said sleeve defining a passage between said sleeve and said tubular support arm that communicates with said opening;
   a shield connected to said second end of said tubular support arm, said shield having an arcuate outer surface with an aperture therethrough, said aperture dimensioned to receive one end of said sleeve;
   an electrical device attached to said second end of said support arm by a mounting bracket, said electrical device being rotatable about a first axis through said mounting bracket and further being rotatable about a second axis through said mounting bracket that is perpendicular to said first axis;
   data cables extending through said tubular support arm, said cables extending through said opening near said second end of said tubular support arm and through said passage in said sleeve for attachment to said electrical device; and
   a cover having an inner arcuate surface mounted to said electrical device to be movable therewith, said cover enclosing said shield with said arcuate outer surface of said shield facing said arcuate inner surface of said cover, said cover having an elongated slot formed in said arcuate inner surface, said sleeve extending through said slot, wherein said shield and said cover are movable relative to each other and said shield and cover form a cavity containing said data cables and connections to said electrical device.

2. A device as defined in claim 1, wherein said sleeve includes an enlarged area defining an inner cavity between said sleeve and said tubular support arm.

3. A device as defined in claim 2, wherein said sleeve is comprised of a first sleeve section and a second sleeve section.

4. A device as defined in claim 3, wherein said shield is pivotally mounted to said mounting bracket such that said shield is rotatable about said first axis relative to said cover and said mounting bracket.

5. A device as defined in claim 4, wherein said cover is mounted to said mounting bracket and is movable therewith relative to said support arm.

6. A device as defined in claim 5, wherein said shield and said cover are rotatable together relative to said support arm about said second axis.

7. A device as defined in claim 1, wherein said electrical device is a video monitor.

8. A device as defined in claim 7, wherein said electrical device is movable relative to said support arm between a first position and a second position.

9. A cover assembly for enclosing data connections on a monitor that is mounted to a tubular support arm that has data cables extending therethrough, said cover assembly comprised of:
   a sleeve surrounding said tubular support arm and covering said data cables where said cables exit said tubular support arm, said sleeve defining a passage between said sleeve and said tubular support arm for a portion of said cables to extend therethrough;
   a shield connected to said second end of said tubular support arm, said shield having an arcuate outer surface with an aperture therethrough, said aperture dimensioned to receive one end of said sleeve; and
   a cover having an inner arcuate surface mounted to said monitor to be movable therewith, said cover enclosing said shield with said arcuate outer surface of said shield facing said arcuate inner surface of said cover, said cover having an elongated slot formed in said arcuate inner surface, said sleeve extending through said slot, wherein said monitor is rotatable about a first axis and further is rotatable about a second axis that is perpendicular to said first axis, and a connection between said data cables and said monitor are contained within a cavity defined by said shield and said cover.

10. A cover assembly as defined in claim 9, wherein said sleeve includes an enlarged area defining an inner cavity between said sleeve and said tubular support arm.

11. A cover assembly as defined in claim 10, wherein said sleeve is comprised of a first sleeve section and a second sleeve section.

12. A cover assembly as defined in claim 9, further comprising a mounting bracket attached to said electrical device.

13. A cover assembly as defined in claim 12, wherein said shield is pivotally mounted to said mounting bracket such that said shield is rotatable about said first axis relative to said cover and said mounting bracket.

14. A cover assembly as defined in claim 13, wherein said cover is mounted to said mounting bracket and is movable therewith relative to said support arm.

15. A cover assembly as defined in claim 14, wherein said shield and said cover are rotatable together about said second axis.

* * * * *